United States Patent
Karl et al.

(10) Patent No.: US 6,218,572 B1
(45) Date of Patent: *Apr. 17, 2001

(54) PREPARATION OF N-Z-PROTECTED N-METHYLATED AMINO ACIDS

(75) Inventors: Ulrich Karl, Ludwigshafen; Stefan Müller, Speyer; Bernd de Potzolli, Bad Dürkheim, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/737,740
(22) PCT Filed: May 9, 1995
(86) PCT No.: PCT/EP95/01752
  § 371 Date: Nov. 19, 1996
  § 102(e) Date: Nov. 19, 1996
(87) PCT Pub. No.: WO95/32180
  PCT Pub. Date: Nov. 30, 1995

(30) Foreign Application Priority Data

May 19, 1994 (DE) .................................. 44 17 478

(51) Int. Cl.$^7$ .................................................. C07C 227/18
(52) U.S. Cl. ............................................................ 562/444
(58) Field of Search ........................................... 562/444

(56) References Cited

U.S. PATENT DOCUMENTS 4,250,085  2/1981  Atherton et al. .................. 260/112.5

FOREIGN PATENT DOCUMENTS 28 55 786  12/1978  (DE) .
90/06914   6/1990   (WO) .

OTHER PUBLICATIONS

Greene, Protective Groups in Organic Synthesis pp. 407, 412, 441, 442, 1991.*
Mcomie, Protective Groups in Organic Chemistry pp. 56–59, 1973.*
Green, Protective Groups in Organic Synthesis pp. 315–316, 327–330, 335–338, 441–444, 1991.*
Green Protective Groups in Organic Synthesis 2nd Ed pp. 335–340, 1991.*
Synthetic Comm., 24(17), 2429, 1994.*
McOmie, Protective Groups in Organic Chemistry pp. 56–57, 1973.*
Wenger, *Angew. Chem.*, vol. 97, p. 88–96.
Pettit et al., *J. Nat. Prod.*, 1981, vol. 44, pp. 482–485, Jul./Aug. 1981.
Cheung et al., *Can. J. Chem.*, vol. 55, 1977. pp. 906–910.
Olsen, *J. Org. Chem.*, vol. 35, No. 6, 1970, pp. 1912–1915.
Fieser & Fieser, Reagents for Organic Synthesis vol. 1, 110 Wiley 1967.
Houben–Weyl vol. XV/a, 64.

* cited by examiner

*Primary Examiner*—Robert Gerstl
(74) *Attorney, Agent, or Firm*—Keil & Weinkauf

(57) ABSTRACT

A process for preparing N-protected N-alkylated amino acids of the formula I:

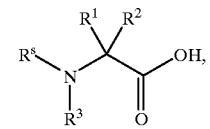

in which the substituents have the meanings stated in the description, comprises mixing a compound of the formula II

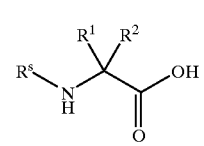

with a solution of potassium tert-butanolate in a non-protic organic solvent, and subsequently adding a $C_{1-2}$-alkyl halide.

4 Claims, No Drawings

PREPARATION OF N-Z-PROTECTED N-METHYLATED AMINO ACIDS

The present invention relates to a novel process for preparing N-protected N-alkylated amino acids. N-alkylated amino acids are important constituents of highly biologically active peptides. Examples of such peptides are cyclosporins (Wenger; Agnew. Chem. 1985, 97, 88) and dolastatins (G. Pettit; J. Nat. Prod. 1981, 44, 482).

The preparation of N-monoalkylated amino acids without using N-protective groups has achieved no practical significance.

The processes described in the literature require excesses of reagents which are costly and difficult to handle (silver oxide, sodium hydride) (DE 2855786; Benoiton; Can. J. Chen. 1977, 55, 906). In addition, the esterification of the acid functionality (Olsen, J. Org. Chem. 1970, 35, 1912) which often occurs at the same time is unwanted and troublesome. N-protected N-alkylated amino acid derivatives are particularly advantageous for use in peptide chemistry because the alkylated amino group cannot react and the acid functionality does not have to be unblocked.

The most practicable process presented to date is that of Runge (WO 90/06914), wherein t-butyloxycarbonyl-protected amino acids are mixed with alkyl iodide, and the methylation takes place after addition of potassium tert-butanolate.

However, the protective group chosen for the process described in WO 90/06914 is not optimal for preparing larger amounts of N-protected N-alkylated amino acids. When the benzyloxycarbonyl protective group (abbreviated to Z hereinafter) is used in place of the t-butyloxycarbonyl group under the conditions of WO 90/06914, only a very moderate yield of the required N-alkylated amino acid is obtained, in addition to many byproducts.

The use of the Z protective group under the conditions described by Runge has not hitherto been described, presumably because it is evident from the relevant literature (Fieser & Fieser; Reagents for Organic Synthesis Vol. 1, 110 Wiley 1967; Houben-Weyl Vol. XV/1, 64) that the Z protective group is readily hydrolyzed under alkaline conditions.

We have found, surprisingly, that the required product can be obtained in very good yield and purity when the reaction is carried out suitably.

The present invention relates to a process for preparing N-proctected N-alkylated amino acids of the formula I:

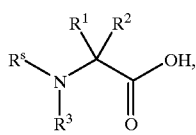

I where $R^s$ is a conventional protective group in peptide synthetis, $R^1$ is the side chain of a proteinogenous amino acid or derivative thereof, $R^2$ is hydrogen, alkyl, alkenyl, alkynyl, aryl or hetaryl and $R^3$ is $C_{1-2}$-alkyl which comprises mixing a compound of the formula II:

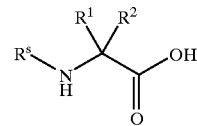

II where $R^1$, $R^2$ and $R^s$ have the abovementioned meanings, with a solution of potassium tert-butanolate in a non-protic organic solvent and subsequently adding a $C_{1-2}$-alkyl halide.

The substituents in formula I preferably have the following meanings:

$R^1$ the residue of a proteinogenous amino acid, in particular H, $CH_3$, $CH_2-CH_2-CH_3$, $CH(CH_3)-CH_2-CH_3$, $CH_2-CH-(CH_3)_2$, $CH_2-C_6H_5$, $CH_2-C_6H_4O-C(CH_3)_3$, $CH_2-C_6H_4OCH_2-C_6H_5$, $CH_2-O-CH_3$, $CH_2-O-C(CH_3)_3$, $CH_2-O-Si(CH_3)_3$, $CH_2-O-CH_2-C_6H_5$, $CH_2-C_6H_4O-Si(CH_3)_3$, $CH(CH_3)-O-CH_3$, $CH(CH_3)-O-C(CH_3)_3$, $CH(CH_3)-O-Si(CH_3)_3$, $CH(CH_3)-O-CH_2-C_6H_5$, $CH_2-S-C(C_6H_5)_3$, $CH_2-S-CH(C_6H_5)_2$, $CH_2-S-CH_2-C_6H_5$, $CH_2CH_2CH_2CH_2N-(CO)_2C_6H_4$, particularly $CH-(CH_3)_2$, $R^2$ H, $C_{1-4}$-alkyl, in particular $CH_3$, $CH_2-CH_3$, $CH_2-CH_2-CH_3$, $CH(CH_3)-CH_2-CH_3$, $CH_2-CH_2-CH_2-CH_3$, $CH_2-CH-(CH_3)_2$, $C(CH_3)_3$, $CH_2-CH=CH_2$, $CH_2-C\equiv CH$, $C_6H_5$, $C_6H_4CH_3$, $R^3$ methyl, $R^S$ $COOCH_2-C_6H_5(=Z)$, $COOC(CH_3)_2-C_6H_5(=DMZ)$, $COOCH_2-C_6H_4(4-Br)$ $(=BZ)$, $COOCH_2-C_6H_4(4-Cl)(=CZ)$, $COOCH_2-C_6H_4(3-Cl)(=3CZ)$, $COOCH_2-C_6H_4(2-Cl)$ $(=2CZ)$, $COOCH_2-C_6H_4(4-OCH_3)$ $(=MOZ)$, $COOCH_2-C_6H_4(4-NO_2)(=NZ)$, $COOCH_2-C_6H_4(2-NO_2)$ $(=2NZ)$, $COOCH_2-C_6H_4(4-OCOCH_3)(=AcOZ)$.

The particularly preferred protective group is Z.

The reaction according to the invention is expediently carried out under an inert protective gas such as helium or argon. It is particularly advantageous to use nitrogen.

Suitable solvents for the reaction are non-protic solvents, in particular tetrahydrofuran, 1,2-dimethoxyethane, diethoxymethane, dioxane, dichloromethane, trichloromethane, tetrachloromethane and N,N-dimethylethyleneurea, N,N-dimethylpropyleneurea and N-methylpyrrolidone.

Tetrahydrofuran is preferably used.

The bases used are sodium t-butanolate or potassium t-butanolate. Potassium t-butanolate is preferably employed. From 2.2 to 10, preferably 3.5 to 6, equivalents of the base are used, based on II.

Suitable alkylating agents are methyl and ethyl bromides and, in particular, methyl and ethyl iodides. From 1.2 to 6, in particular 2.5, equivalents of the alkylating agent are used, based on II.

The reaction takes place at from −40° C. to +1000° C. It is advantageously carried out at from −10° C. to +20° C.

The reaction can be worked up by distillation, extraction, crystallization, chromatography or a combination thereof. It is preferred to carry out an extraction after acidification and subsequently to crystallize the compound I.

The acidification can be carried out with acids such as hydrochloric acid, sulfuric acid, phosphoric acid, hydrobromic acid, acetic acid, methanesulfonic acid. Sulfuric acid is preferably used. Extractants which can be used are water-immiscible solvents such as pentane, hexane, heptane, octane, petroleum ether, ethyl acetate, diethyl ether, diisopropyl ether, methyl t-butyl ether, dichloromethane, xylene, chloroform, tetrachloromethane, benzene, toluene, particularly preferably toluene. The crystallization can take place from organic solvents such as pentane, hexane, heptane, octane, petroleum ether, ethyl acetate, dichloromethane, chloroform, tetrachloromethane, benzene, toluene, xylene, acetone, 2-butanone, methanol, ethanol, n-propanol, isopropanol, diethyl ether, diisopropyl ether, methyl t-butyl ether and mixtures thereof, preferably toluene and toluene/heptane mixtures. If the amino acids contain other reactive groups, for example cysteine, serine, tyrosine, lysine, threonine, these must be protected during the reaction.

Particular advantages of the process are that
1) low-cost starting materials with advantageous handling properties are used (Z-amino acids),
2) no simultaneous esterification takes place,
3) the yield is much greater than in processes disclosed in the literature,
4) the isolated product has high purity and can be used without further purification for subsequent reactions, and
5) no racemization takes place.

EXAMPLE 1

(S)-Z-N-Methylisoleucine 19.6 g of potassium tert-butanolate dissolved in 100 ml of THF were added over the course of 1 h to a solution of 13.25 g of (S)-Z-isoleucine and 17.75 g of methyl iodide in 70 ml of THF at −10–0° C. Then 18.9 g of methyl iodide were added in such a way that the temperature remained between 0 and 5° C. The mixture was subsequently stirred at −10° C. for 2 h and then at 20° C. for 2 h. The reaction was stopped by adding 200 ml of water. The organic phase was separated off, and the aqueous phase was extracted with 100 ml of toluene. The combined organic phases were discarded. The aqueous phase was acidified and extracted with methylene chloride. The methylene chloride phase was evaporated to dryness. The crude product obtained in this way was recrystallized from toluene/heptane. 7.5 g of product with a purity>96% were isolated.

Melting point 50.5–54.3° C.

The following were prepared as in Example 1:
2. (S)-Z-N-Methylvaline
   Yield: 85%; Purity: 99% (HPLC)
   Melting point: 69.6–71.2° C. $[\alpha]_D$=−85.0° (c=0.99 in $CH_3OH$)
3. (S)-Z-N-Methylvaline
   (Methyl bromide was used in place of methyl iodide)
   Yield: 73.5%; Purity 98% (HPLC)
4. (S)-Z-N-Methylphenylalanine
   Yield: 81%; Purity 97.4% (HPLC)
   Melting point: 66.5–68.0° C. $[\alpha]_D$=−65.1° (c=1.0 in $CH_2Cl_2$)
5. (S)-Z-N-Methylserine(tbu)
   Yield:>95%; Purity 96% (HPLC)
   $^1$H-NMR [270 MHz, $CDCl_3$]: 1.2 (9H), 3.0 (3H),3.7–3.9 (2H), 4.65–4.8 (2H), 5.2 (2H), 7.3 (5H), 9.8 [1H]

The following compounds can be prepared in a similar way:
(S)-Z-N-Methylalanine; (R)-Z-N-Methylalanine;
(+/−)-Z-N-Methylalanine;
(S)-Z-N-Methylleucine; (R)-Z-N-Methylleucine;
(+/−)-Z-N-Methylleucine;
(S)-Z-N-Methylthreonine(O-benzyl);
(R)-Z-N-Methylthreonine(O-benzyl);
(+/−)-Z-N-Methylthreonine(O-benzyl);
Z-N-Methylglycine;
(S)-Z-N-Methylmethionine; (R)-Z-N-Methylmethionine;
(+/−)-Z-N-Methylmethionine;
(S)-Z-N-Methylcysteine(S-benzyl);
(R)-Z-N-Methylcysteine(S-benzyl);
(+/−)-Z-N-Methylcysteine(S-benzyl);
Z-N-Ethylglycine.

We claim:
1. A process for preparing N-protected N-alkylated amino acids of the formula I:

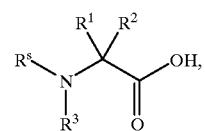

where
$R^s$ is an unsubstituted or substituted carbobenzoxy radical,
$R^1$ is the side chain of a proteinogenous amino acid or derivative thereof,
$R^2$ is hydrogen, alkyl, alkenyl, alkynyl, aryl or hetaryl and
$R^3$ is $C_{1-2}$-alkyl which comprises mixing a compound of the formula II:

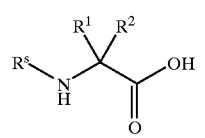

where $R^1$, $R^2$ and $R^s$ have the abovementioned meanings, with a solution of the base potassium tert-butanolate or the base sodium tert-butanolate in a non-protic organic solvent and subsequently adding a $C_{1-2}$-alkyl halide alkylating agent wherein from 2.2 to 10 equivalents of the base is used, based on II.

2. The process of claim 1, wherein methyl iodide or bromide is used as the alkylating agent.

3. The process of claim 2, wherein $R^s$ is $COOCH_2$—$C_6$—$H_5$.

4. The process of claim 1, wherein from 3.5 to 6 equivalents of the base are used.

* * * * *

UNITED STATES PATENT AND TRADEMARK OFFICE
CERTIFICATE OF CORRECTION

PATENT NO. : 6,218,572 B1
DATED : April 17, 2001
INVENTOR(S) : Karl et al.

It is certified that error appears in the above-identified patent and that said Letters Patent is hereby corrected as shown below:

Column 4, claim 1,
Line 34, "carbobenzoxy" should be -- benzyloxy carbonyl --.

Signed and Sealed this

Sixth Day of November, 2001

Attest:

*Nicholas P. Godici*

NICHOLAS P. GODICI
*Attesting Officer*  *Acting Director of the United States Patent and Trademark Office*